US00PP28089P2

(12) United States Plant Patent
Danziger

(10) Patent No.: US PP28,089 P2
(45) Date of Patent: Jun. 6, 2017

(54) ***CALIBRACHOA* PLANT NAMED 'DANOGLINT'**

(50) Latin Name: *Calibrachoa hybrida*
Varietal Denomination: DANOGLINT

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 14/999,064

(22) Filed: Mar. 25, 2016

(51) Int. Cl.
*A01H 5/02* (2006.01)

(52) U.S. Cl.
USPC ..... Plt./413

(58) Field of Classification Search
USPC ..... Plt./413
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Calibrachoa* cultivar named 'DANOGLINT' is disclosed, characterized by a well branched, mounded plant habit. Plants produce an abundance of large purple flowers with darker purple veins and violet stripes between the petals, with a light yellow center and throat. The new variety is a *Calibrachoa*, normally produced as an outdoor garden or container plant.

2 Drawing Sheets

Figure 1:
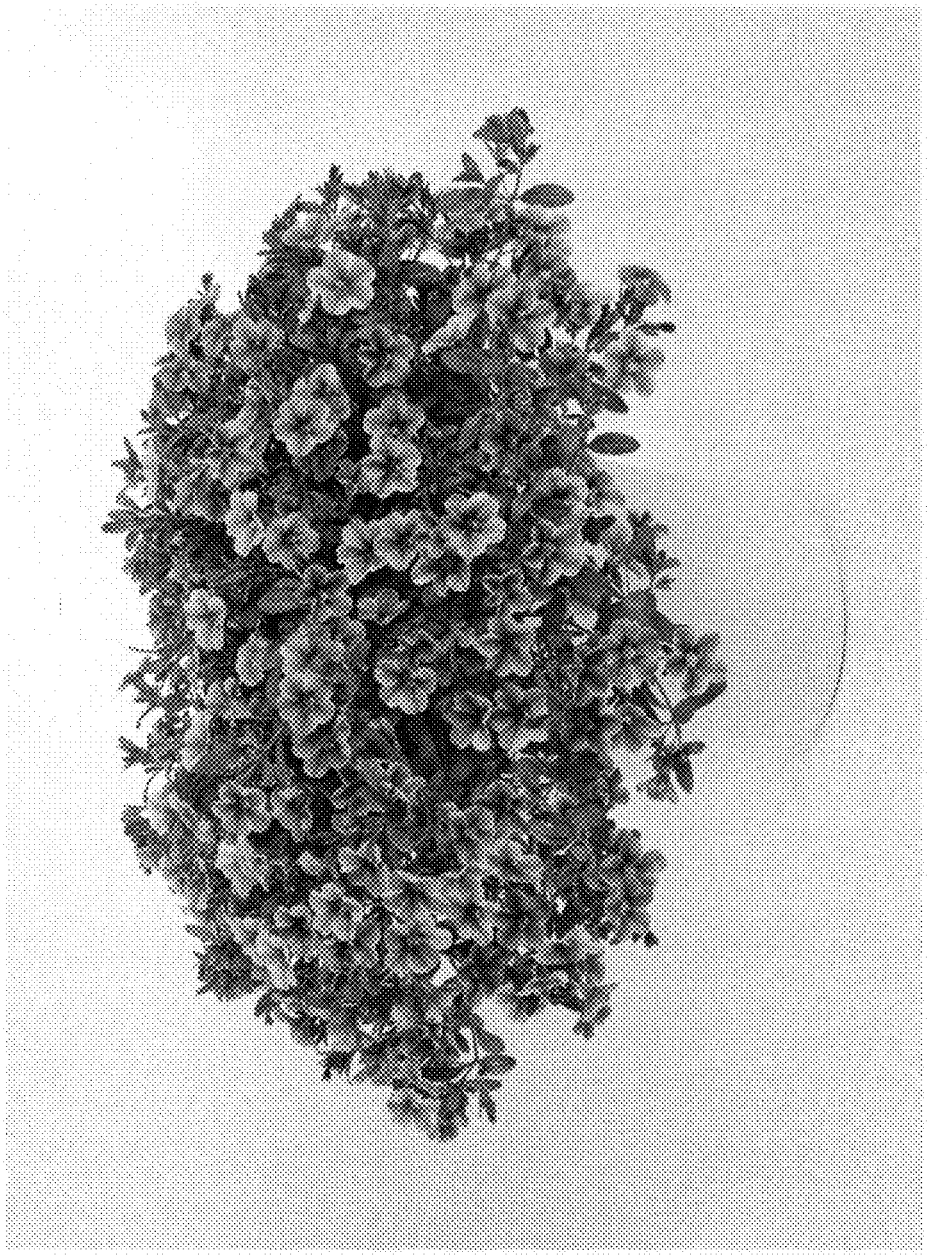

Latin name of the genus and species: *Calibrachoa hybrida.*

Variety denomination: 'DANOGLINT'.

BACKGROUND OF THE INVENTION

The new *Calibrachoa* cultivar is a product of a planned breeding program conducted by the inventor, Gavriel Danziger in Moshav Mishmar Hashiva, Israel. The objective of the breeding program was to produce new *Calibrachoa* varieties. The cross resulting in this new variety was made during March of 2013.

The seed parent is the unpatented, propriety variety referred to as *Calibrachoa* 'cv. 12-3202'. The pollen parent is the unpatented, propriety variety referred to as *Calibrachoa* 'cv. 12-3181'. The new variety was discovered in November of 2013 by the inventor in a group of seedlings resulting from the 2013 crossing, in a greenhouse in Moshav Mishmar Hashiva, Israel.

Asexual reproduction of the new cultivar 'DANOGLINT' was first performed by terminal vegetative cuttings during November of 2013, at a greenhouse in Moshav Mishmar Hashiva, Israel. Subsequent propagation by has shown that the unique features of this cultivar are stable and reproduced true to type in more than 20 successive generations.

SUMMARY OF THE INVENTION

The cultivar 'DANOGLINT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANOGLINT' These characteristics in combination distinguish 'DANOGLINT' as a new and distinct *Calibrachoa* cultivar:

1. Mounded growth habit.
2. Very well-branched

3. Flower color is purple with darker purple veins and violet stripes between the petals, with a light yellow center and throat.
4. Large flower size.
5. Abundance of flowers.

PARENT COMPARISON

Plants of the new cultivar 'DANOGLINT' are similar to plants of the seed parent, *Calibrachoa* 'cv. 12-3202' most horticultural characteristics, however, plants of the new cultivar 'DANOGLINT' differ in the following;

1. The parent has a trailing growth habit, the new variety is mounded
2. Moderate branching in the parent variety, the new variety is very well branched
3. Parent flower color is pink, the new variety flower color is purple with darker purple veins and violet stripes between the petals, with a light yellow center and throat.
4. Flowers are medium sized, the new variety has a larger flower
5. Moderate quantity of flowers, the new variety has an abundance of flowers.

Plants of the new cultivar 'DANOGLINT' are similar to plants of the pollen parent, *Calibrachoa* 'cv. 12-3181' most horticultural characteristics however, plants of the new cultivar 'DANOGLINT' differ in the following;

1. The parent has a semi-trailing growth habit whereas the new variety is mounded
2. The new variety has more branches than the pollen parent.
3. Parent flower color is pink/red with white stripes, the new variety flower color is purple with darker purple veins and violet stripes between the petals, with a light yellow center and throat.
4. The new variety has a larger flower than the pollen parent.

5. Moderate quantity of flowers, the new variety has an abundance of flowers.

COMMERCIAL COMPARISON

Plants of the new cultivar 'DANOGLINT' can be compared to the patented commercial variety *Calibrachoa* 'DANOA60' U.S. Plant Pat. No. 22,987. These varieties are similar in most horticultural characteristics; however, 'DANOGLINT' differs in the following:

1. Growth habit of the comparison variety is semi-trailing, while the new variety has a mounded growth habit.
2. The comparison variety is moderately well branched, while the new variety is very well branched.
3. Flower color of the comparison variety is violet with a white throat, while flower color of the new variety is purple with darker purple veins and violet stripes between the petals, with a light yellow center and throat.
4. Flower size of the comparison variety is larger than that of the new variety.
5. The comparison variety has fewer flowers per plant than the new variety.

Plants of the new cultivar 'DANOGLINT' can also be compared to the unpatented commercial variety *Calibrachoa* 'DANOA20'. These varieties are similar in most horticultural characteristics; however, 'DANOGLINT' differs in the following:

1. Growth habit of comparison variety is semi-trailing, while the new variety has a mounded growth habit.
2. The comparison variety is moderately branched, while the new variety is very well branched.
3. Flower color of comparison variety is blue with a yellow throat, while flower color of the new variety is purple with darker purple veins and violet stripes between the petals, with a light yellow center and throat.
4. Flowering time of the comparison variety is later in the season than the new variety.
5. The comparison variety has fewer flowers per plant than the new variety.

BRIEF DESCRIPTION OF THE PHOTOGRAPHS

The accompanying photograph in FIG. 1 illustrates in full color a typical plant of 'DANOGLINT' grown in a greenhouse, in Moshav Mishmar Hashiva, Israel.

Figure 2:
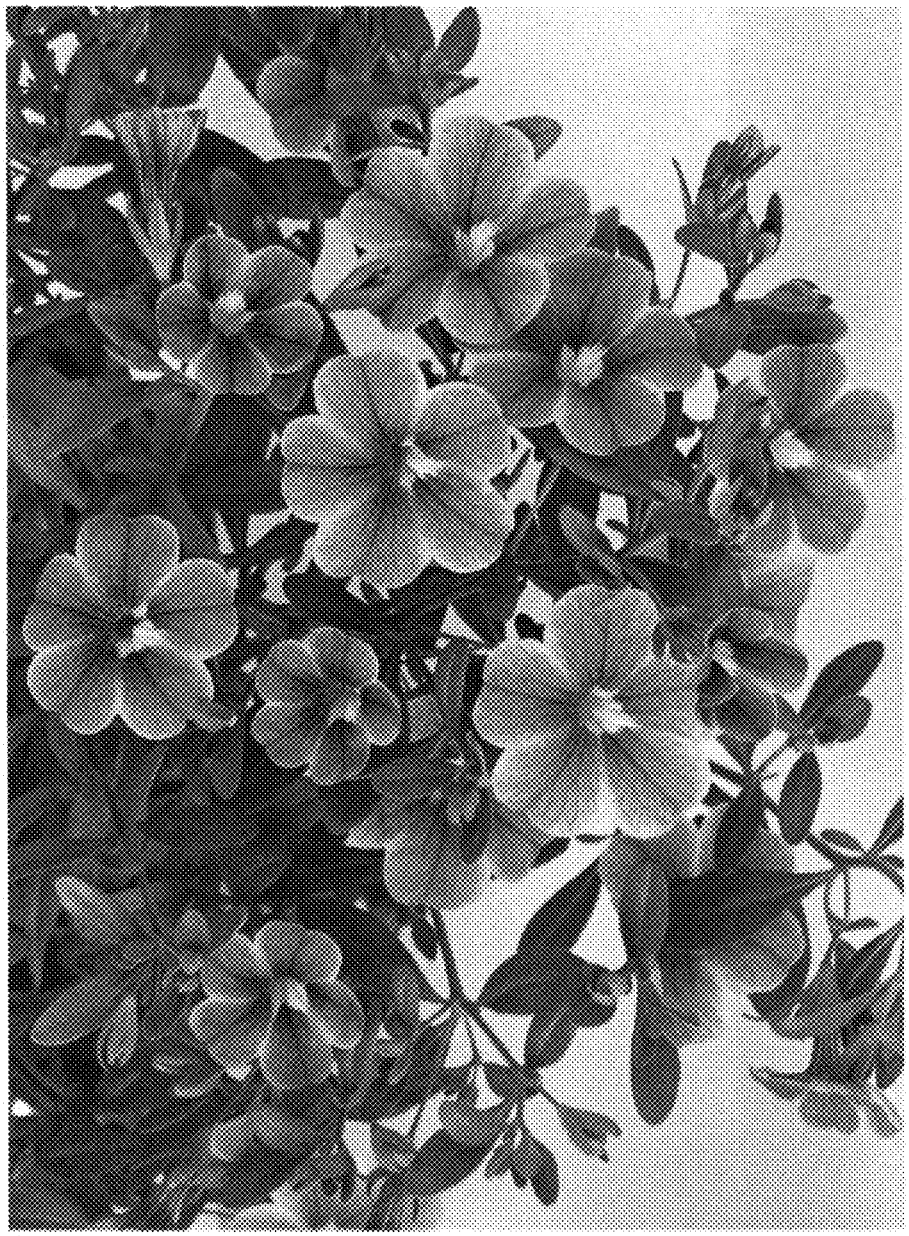

FIG. 2 illustrates in full color a typical mature flower of 'DANOGLINT' during Spring. Age of the plant photographed is approximately 60 days from a rooted cutting in a 20 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DANOGLINT' plants grown in greenhouse in Moshav Mishmar Hashiva, Israel, under natural lighting. Measurements were taken during April of 2015. The plants were approximately 45 days from a rooted cutting in a 13 cm pot. The growing temperature ranged from 18° C. to 35° C. during the days, 15° C. to 25° C. during the nights. Measurements and numerical values represent averages of typical plant types.

Botanical classification: *Calibrachoa hybrida* 'DANOGLINT'.

PROPAGATION

Time to initiate roots: 10-14 days at approximately 20-22° C.

PLANT

Growth habit: Mounded.
Pot size of plant described: 13 cm.
Height: About 14 cm to top of flowering plane.
Plant spread: About 50 cm.
Growth rate: Medium.
Branching characteristics: Very well branched.
Length of primary lateral branches: About 25 cm.
Diameter of lateral branches: about 0.2 cm.
Quantity of primary lateral branches: 8.
Characteristics of primary lateral branches:
*Form.*—Cylindrical.
*Diameter.*—About 0.3 cm.
*Color.*—RHS Brown 200 B.
*Texture.*—Slightly pubescent.
*Strength.*—Strong.
Internode length: About 2 cm.
Root description: Fibrous.

FOLIAGE

Leaf:
*Arrangement.*—Alternate.
*Quantity.*—Approximately 70 per branch.
*Average length.*—4.5 cm.
*Average width.*—1.6 cm.
*Shape of blade.*—Elliptic.
*Apex.*—Rounded.
*Base.*—Acute.
*Margin.*—Entire.
*Texture of top surface.*—Velvety.
*Texture of bottom surface.*—Velvety.
*Pubescence.*—Pubescent.
*Color.*—Young foliage upper side: RHS Green N 137 B. Young foliage under side: RHS Yellow-Green 147 B. Mature foliage upper side: RHS Green 137 A. Mature foliage under side: RHS Yellow-Green 147 B.
*Venation.*—Type: Pinnate. Venation color upper side: RHS Yellow-Green 146 B. Venation color under side: RHS Yellow-Green 146 C.
*Petiole.*—Length: about 0.5 cm. Diameter: about 0.2 cm. Color: RHS Yellow-Green 146 B. Texture: Velvety.

FLOWER

Natural flowering season: Spring, Summer and Autumn.
Days to flowering from rooted cutting: About 40 days.
Inflorescence and flower type and habit: Axillary, single flower, salverform shape, upward and outwardly facing.
Rate of flower opening: 3 to 4 days from bud to fully opened flower.

Flower longevity on plant: 4 to 7 days.
Approximate quantity of flowers per plant: About 100.
Persistent or self-cleaning: Self-cleaning.
Bud:
*Shape*.—Tubular.
*Length*.—About 2.5 cm.
*Diameter*.—About 0.8 cm.
*Color*.—RHS Violet 83 B.
Flower size:
*Diameter*.—About 3.6 cm.
*Length*.—About 2.5 cm.
*Flower tube diameter at distal end*.—About 0.8 cm.
*Flower tube diameter at proximal end*.—About 0.3 cm.
Petals:
*Length from throat*.—About 1.5 cm.
*Width*.—About 1.6 cm.
*Quantity*.—5.
*Texture*.—Velvety.
*Apex*.—Cordate.
*Margin*.—entire.
Color:
*When opening*.—Upper surface: RHS Purple 77 A with Violet stripes between the petals RHS Violet N 87 C and a light Yellow center RHS Yellow 9 C. Lower surface: RHS Violet N 87 C with Purple veins RHS Purple 79 B.
*Fully opened*.—Upper surface: RHS Purple 77 A with Purple veins RHS Purple 79 B and Violet stripes between the petals RHS Violet N 87 C and a light Yellow center RHS Yellow 9 C. Lower surface: RHS Violet N 87 D with Purple veins RHS Purple 79 B. Flower throat (inside): RHS Yellow 9 C. Flower throat, vein: RHS Purple 79 B. Flower tube (outside): RHS Yellow 9 C. Flower tube, vein: RHS Purple 79 B. Petal color, fading to: Purple-Violet N 82 A with Purple veins RHS Purple 79 C and Violet stripes between the petals RHS Purple-Violet N 82 D and a light Yellow center RHS Yellow 5 C.
Calyx/sepals:
*Quantity per flower*.—5.
*Shape*.—Elliptic.
*Length*.—About 1.5 cm.
*Width*.—About 0.6 cm.
*Apex*.—Acute.
*Base*.—Fused.
*Margin*.—Entire.
*Texture*.—Velvety.
*Color*.—Upper Surface: RHS Green 137 A. Lower Surface: RHS Green 137 B.
Peduncle: Not present.
Pedicel:
*Length*.—About 2 cm.
*Diameter*.—About 0.1 cm.
*Color*.—RHS Yellow-Green N144 A.
*Orientation*.—45 degrees.
Fragrance: None.

REPRODUCTIVE ORGANS

Stamens:
*Number*.—5.
*Filament length*.—About 1 cm.
Anthers:
*Length*.—About 0.1 cm.
*Shape*.—Rounded.
*Color*.—RHS Yellow 13 B.
*Pollen*.—Color: RHS Yellow 13 C. Quantity: moderate amount.
Pistil:
*Number*.—1.
*Length*.—About 1.2 cm.
*Style*.—Length: about 1.0 cm. Color: RHS Yellow-Green 144 B.
*Stigma*.—Shape: Rounded. Color: RHS Yellow-Green 144 A. Ovary Color: RHS Yellow-Green 144 C.

OTHER CHARACTERISTICS

Seeds and fruits: About 30 brown, rounded seeds of about 0.5 mm diameter, per one brown, conical capsule.
Disease/pest resistance: Typical to known *Calibrachoa* varieties. Neither resistance nor susceptibility to the normal diseases and pests of *Calibrachoa* have been observed. Pests common to *Calibrachoa* include Aphids and thrips. Typical diseases are *Botrytis* and *Pythium*.
Temperature tolerance: 5° C. to 30° C.
Drought tolerance: No tolerance for drought.

What is claimed is:

1. A new and distinct cultivar of *Calibrachoa* plant named 'DANOGLINT' as herein illustrated and described.

* * * * *